(12) United States Patent
Auh et al.

(10) Patent No.: US 6,987,002 B2
(45) Date of Patent: Jan. 17, 2006

(54) COMPOSITION FOR DETECTING β-1,3-GLUCAN

(75) Inventors: Joong Hyuck Auh, Seoul (KR); Bu Soo Park, Kwangju (KR); Chang Hun Joo, Pusan (KR); Chong Jin Park, Taejon (KR); Bok Luel Lee, Pusan (KR); Kum Young Lee, Pusan (KR); Seung-Suh Hong, Taejon (KR); Hyun-Soo Lee, Seoul (KR)

(73) Assignee: Samyang Genex Corporation, Seoul (KR)

( * ) Notice: Subject to any disclaimer, the term of this patent is extended or adjusted under 35 U.S.C. 154(b) by 190 days.

(21) Appl. No.: 09/938,334

(22) Filed: Aug. 23, 2001

(65) Prior Publication Data

US 2002/0197662 A1 Dec. 26, 2002

Related U.S. Application Data

(63) Continuation of application No. PCT/KR01/00106, filed on Jan. 20, 2001.

(30) Foreign Application Priority Data

Jan. 20, 2000 (KR) .......................................... 2000-2542

(51) Int. Cl.
*C12Q 1/26* (2006.01)

(52) U.S. Cl. ......................................... 435/25; 435/259
(58) Field of Classification Search .................. 435/25, 435/6; 514/54; 424/254.1, 274.1; 536/123.12, 536/124, 127

See application file for complete search history.

(56) References Cited

U.S. PATENT DOCUMENTS

| 4,970,152 | A | * | 11/1990 | Ashida et al. | ................. | 435/19 |
| 5,266,461 | A | * | 11/1993 | Tanaka | ....................... | 435/7.21 |
| 5,585,248 | A | * | 12/1996 | Ashida et al. | ................. | 435/25 |
| 6,274,565 | B1 | * | 8/2001 | Katsumi | ....................... | 514/54 |

FOREIGN PATENT DOCUMENTS

| JP | 58-502082 A1 | 12/1983 |
| JP | 63-141598 A1 | 6/1988 |
| JP | 09-131174 A1 | 5/1997 |
| JP | 11-178599 | 7/1999 |

OTHER PUBLICATIONS

Brehelin M. Insect Haemolymph . . . Insect Biochem 19(3)301–307, 1989.*
Asokan R. Activation of Prophenoloxidase in the Plasma and Haemocytes of the Marine Mussel. Developmental and Comparative Immunology 21(1)1–12, 1997.*
Ashida M. Studies on Prophenoloxidase Activation in the Mostquite Aedes aegypti L. Eur J Biochem vol. 89, 507–515, 1990.*
Leonard C. Studies on Prophenoloxidase and Protease Activity of *Blaberus craniifer* Haemocytes. Insect Biochem 15(6)803–810, 1985.*
Brivio M. ProPO System of *Allogamus auricollis* Insecta. Comp Biochem Physiol 113B(2)281–287, 1996.*
Prophenoloxidase Activating System in the Coelomic Fluid of the Redworm, *Lumbricus rubellus*, Yun–Kyung Bahk et al., Korean Journal of Zoology, vol. 38, No. 1, pp. 125–135, Jan. 1995, English Abstract.
Activation of Prophenoloxidase in the Plasma and Haemocytes of the Marine Mussel *Perna viridis Linnaeus*, Rengasamy Asokan et al., Developmental and Comparative Immunology, vol. 21, No. 1, pp. 1–12, 1997.
Immune Response in Insects: The Role of Phenoloxidase in Defense Reactions in Relation to Melanization and Sclerotization, Vassilis J. Marmaras et al., Archives of Insect Biochemistry and Physiology, vol. 31, pp. 119–133, 1996.
Cell Wall Assembly by *Pneumocystis carinii*, Theodore J. Kottom et al., The Journal of Biological Chemistry, vol. 275, No. 51, pp. 40628–40634, Dec. 22, 2000.
Studies on prophenoloxidase activation in the mosquito *Aedes aegypti* L., Masaaki Ashida et al., European Journal of Biochemistry, vol. 89, No 0992, pp. 507–515, 1990.

* cited by examiner

*Primary Examiner*—Ralph Gitomer
(74) *Attorney, Agent, or Firm*—Darby & Darby (57) ABSTRACT

The present invention relates to a composition for detecting an infinitesimal quantity of β-1,3-glucan, a preparation method thereof and a diagnostic kit detecting β-1,3-glucan. The composition of the present invention shows phenoloxidase activity by β-1,3-glucan in the presence of calcium ions. Using the composition of the present invention, a sample is gathered from a specimen, the composition of the present invention and calcium ions are added to the sample, and β-1,3-glucan is detected by measuring phenoloxidase activity.

3 Claims, 8 Drawing Sheets

FIG. 11 ing β-1,3-glucan, a preparation method thereof and a diagnostic kit detecting the same which claims priority to Republic of Korea Application 2000-2542 filed Jan. 20, 2000.

COMPOSITION FOR DETECTING β-1,3-GLUCAN

This is a continuation of international application Ser. No. PCT/KR01/00106, filed Jan. 20, 2001, the entire disclosure of which is hereby incorporated by reference.

TECHNICAL FIELD

The present invention relates to a composition for detecting β-1,3-glucan, a preparation method thereof and a diagnostic kit detecting the same which claims priority to Republic of Korea Application 2000-2542 filed Jan. 20, 2000.

BACKGROUND ART OF THE INVENTION

Among immuno-compromised cancer patients, organ transplantation patients and AIDS patients, increase of systematic fungal infection or infection by protozoa has become a serious medical problem. The death rate due to such infections is increasing. For these immuno-compromised patients, it is important to treat the fungal infection at an early stage of the infection by administering anti-fungal drugs. The early diagnosis, however, is a difficult task at present. Also many AIDS patients die of Pneumonia by Pneumocystis carinii infection. Recently, it has been reported that β-1,3-glucan exists as a cell wall component of Pneumocystis carinii (Kottom et al., J. Biol. Chem. (2000), 275(51), pp. 40628–34).

To diagnose a fungal infection in immuno-compromised patients, the standard method in mycology, i.e., a method wherein blood is drawn from a patient and cultivated to diagnose the fungal infection has been used. The method has a shortcoming in that the treatment may not be done on time since the result of the diagnosis can be obtained only after 2–5 days. Recently, methods of using the antigens or the metabolites of the fungus have been suggested. However, in the latter case, there is a difficulty in analyzing all of the metabolites, as well as low sensitivity and low accuracy of the diagnosis due to the frequent mutation of the metabolites. For these reasons, research has been widely performed to find a system to recognize accurately the infinitesimal amount of β-1,3-glucan existing in the patient's blood at the early stage of fungal infection.

In the meantime, if the fungal infection occurs during the breeding of lobster, fish or clams, it could cause a severe economic damage to the aquiculture industry since most of the infected fishery may die. Even in this case, if an early diagnosis could be made, the lives of these aquatic animals could be saved if appropriate actions are taken to increase the efficiency of the aquiculture.

Melanin formation in insects is initiated by the oxidation of phenolic compounds existing in the body. Phenoloxidase acting in this process exists in the insect's body as a prophenoloxidase in ordinary times, and the prophenoloxidase is converted to phenoloxidase as the final activated form by the stimulus of the final product of the prophenoloxidase chain reaction. The activation of prophenoloxidase is reported to be initiated by β-1,3-glucan, lipopolysaccharide, peptidoglycan and other cell wall components of the microorganisms.

Prophenoloxidase exists in the body of holometabola and is activated to phenoloxidase by the cascade reaction that is initiated by either β-1,3-glucan or lipopolysaccharide. The reaction system composed of a series of cascade reaction steps is activated easily by foreign pathogens or other molecules from outer system, or inherent factors induced by the degranulation reaction of the insect's own hemocytes. As a result, prophenoloxidase is converted to phenoloxidase to produce melanin by using catecholamines. Therefore, it has been difficult to carry out this reaction system under in vitro conditions.

In U.S. Pat. No. 4,970,152, Ashida and co-workers have suggested a method for determining peptidoglycan or β-1,3-glucan by using a composition comprising a fraction obtained from plasma of silkworm larvae and capable of reacting specifically with β-1,3-glucan or peptidoglycan but not with endotoxin In this patent a composition capable of reacting specifically with β-1,3-glucan has been obtained by removing the substance that reacts with peptidoglycan by affinity chromatography.

Ashida has also reported in Eur. J. Biochem, 188, 507–515(1990) that the divalent ion plays a crucial role in the activation of prophenoloxidase while presenting a composition, separated from mosquito larvae, that recognize β-1,3-glucan.

U.S. Pat. No. 5,266,461 discloses a reagent for determining β-1,3-glucan comprising limulus amebocyte lysate. There is a problem of using this method, however, since limulus is classified as a protected species in most of the countries.

SUMMARY OF THE INVENTION

The present invention relates to a composition for detecting β-1,3-glucan.

The present invention further relates to a preparation method of a composition for detecting β-1,3-glucan.

The present invention also relates to a method of detecting β-1,3glucan.

The present invention still further relates to a diagnostic kit for detecting β-1,3-glucan.

DETAILED DESCRIPTION OF THE PREFERRED EMBODIMENTS

The present invention relates to a composition for detecting β-1,3-glucan in a test sample, a preparation method thereof and a diagnostic kit for detecting β-1,3-glucan.

As used herein, the term "phenoloxidase system" refers to a system that activates to a phenoloxidase by β-1,3-glucan in insects.

As used herein, the term "phenoloxidase composition" refers to a composition which comprises all or some components of the phenoloxidase system and exhibits phenoloxidase activity by β-1,3-glucan in the presence of calcium ions.

The present invention relates to a composition that shows phenoloxidase activity by β-1,3-glucan in the presence of calcium ions. The phenoloxidase composition in the present invention includes all or some components of the phenoloxidase system in insects and includes prophenoloxidase, for example.

Also the present invention relates to a composition for detecting β-1,3-glucan, preferably the minimum down to 20 pg/ml.

The composition for detecting β-1,3-glucan of the present invention can be used to diagnose infections of fungus such as Candida and/or protozoa such as Pneumocytis carinii.

As used herein, the term "an insect" or "insects" refers to an insect or insects that has a phenoloxidase system in the body, and preferably a holometabola insect. The examples of insect include those belonging to Crustaceans such as lobsters and shrimps and Coleoptera, and more preferably Tenebrionidae and Scarabaeidae orders of Coleoptera.

Also the present invention relates to a preparation method of a composition exhibiting phenoloxidase activity by β-1,3-glucan in the presence of calcium ions. According to the method in the present invention, the phenoloxidase composition that is activated by β-1,3-glucan is isolated by using a mixture of plasma and hemocyte lysate as a sample, and by prohibiting the physiological activity of calcium ions during the separation process.

Therefore, the method in the present invention includes a step to obtain a sample comprising a mixture of plasma and hemocyte lysate from insects, a step to obtain fractions by treating the sample with a solvent or buffer solution containing a sufficient amount of a chelating agent that can chelate the calcium ions existing in the sample and in the present separation process, and a step to select the fractions exhibiting phenoloxidase activity by β-1,3-glucan in the presence of calcium ions.

Another example of the method of the present invention includes a step to obtain plasma from insects, a step to obtain fractions by treating the plasma with a solvent or buffer solution containing a sufficient amount of a chelating agent that can chelate the calcium ions existing in the plasma and in the present separation process, a step to add the hemocyte lysate or partially purified hemocyte lysate to said fractions, and a step to select the fractions exhibiting phenoloxidase activity by β-1,3-glucan in the presence of calcium ions.

If necessary, whole or partially purified hemocyte lysate can be added to the fraction which exhibits the phenoloxidase activity by β-1,3-glucan in the presence of calcium ions to increase sensitivity of the fraction.

According to the present invention, it has been shown that the phenoloxidase system existing in insects can be activated by the calcium ions as well as by β-1,3-glucan Therefore, to separate the phenoloxidase system from the insects, it is necessary to inhibit the activation of the phenoloxidase system or phenoloxidase composition by calcium ions as well as by β-1,3-glucan. Based on these findings, the present invention provides a method for preparing a composition exhibiting the phenoloxidase activity by β-1,3-glucan in the presence of calcium ions from an insect's hemolymph or both plasma and hemocyte lysate.

The method of preparing a phenoloxidase composition according to the present invention includes obtaining a sample comprising hemolymph or a mixture of plasma and hemocyte lysate in the presence of sufficient amount of chelating agent that can chelate the calcium ions possibly existing in the above sample and in the present separation process to obtain the phenoloxidase composition, obtaining fractions by treating the sample with a solvent or buffer solution containing a sufficient amount of the chelating agent that can chelate the calcium ions existing in the above sample and during the separation process, and selecting the fractions exhibiting phenoloxidase activity by β-1,3-glucan in the presence of calcium ions among the obtained fractions.

In the method of the present invention, an anticoagulant buffer solution that can prevent the coagulation of the hemolymph is preferably used while collecting the sample from the insect. The anticoagulant buffer solution includes any buffer solutions that can prevent the coagulation of the insect's hemolymph, more preferably a citrate buffer solution.

Also according to the present invention, it has been shown that a composition which exhibits the phenoloxidase activity specifically by β-1,3-glucan in the presence of calcium ions can be obtained by using a mixture of insect's plasma and hemocytes. The composition of the present invention enables detection of a concentration of β-1,3-glucan as low as 20 pg/ml in the mixture of insect's plasma and hemocytes The mixture of insect's plasma and hemocytes can be obtained by collecting the hemolymph of insects, separating hemocytes and plasma, lysing the separated hemocytes and mixing the hemocyte lysate with plasma. Another example to obtain the mixture of insect's plasma and hemocytes is adding hemocyte lysate or partially purified hemocyte lysate into partially purified plasma to obtain said mixture. In another method, the mixture of insect's plasma and hemocytes can be obtained from hemolymph by lysing a portion of or all the hemocytes without separating the hemocytes from the hemolymph. For instance, hemolymph or separated hemocytes can be lysed by sonication or high-speed centrifugation.

In the method of the present invention, the process of obtaining the fractions by treating the sample with the solvent or buffer solution containing a chelating agent can be performed by column chromatography, for example.

In the method of the present invention, as a chelating agent which is used to chelate calcium ions in collecting the sample comprising a mixture of plasma and hemocyte lysate from insects and in the separation process to obtain a phenoloxidase composition, any of chelating agents known in the field can be used without limitation, and can be EDTA, EGTA or citric acid, for example. The amount of the chelating agent can be various depending on the conditions of the separation process such as the sample, the kind of column and the kind of solvent, and needs to enough to chelate the calcium ions in the insect sample and during the separation process. Therefore, those of ordinary skill in the field would be able to easily determine the amount of the chelating agent without undue experimentation.

The solvent or buffer solution is not limited in the preparation method according to the present invention, but is preferably that of not more than pH 6.5. In case the pH is higher than 6.5, serine protease, a component involved in the phenoloxidase cascade reaction, can be activated and causes activation of prophenoloxidase into phenoloxidase. It results to make it difficult to obtain the composition according to the present invention.

One of the examples to treat the insect sample with the solvent or buffer solution containing a chelating agent is by column chromatography. A column packed with resin can be loaded with an insect sample, and eluted with the solvent or buffer solution containing a chelating agent to obtain fractions. In the present invention, the composition that can detect β-1,3-glucan specifically down to 20 pg/ml can be purified by column chromatography without any further particular separation process such as affinity chromatography.

The resin that can be used for column chromatography in the present invention is preferably the resin that uses dextran or vinyl as a raw material. For example, Sephadex or Toyopearl can be used.

The composition according to the present invention can be used in diagnosing infection by microorganisms having β-1,3-glucan since it can specifically detect β-1,3-glucan.

Therefore, the present invention relates to a method of diagnosing infection by microorganisms that have β-1,3-glucan. The method of the present invention includes the steps of collecting a sample from a specimen, adding calcium ions and the composition that exhibits phenoloxidase activity by β-1,3-glucan in the presence of calcium ions to the sample and measuring the phenoloxidase activity in the sample. For example, the composition of the present invention which exhibits phenoloxidase activity by β-1,3-glucan in the presence of calcium ions can be prepared by selecting the fraction that can activate phenoloxidase by β-1,3-glucan in the presence of calcium ions from among the fractions obtained by treating the sample, insect plasma and hemocyte lysate, with a solvent containing a sufficient amount of a chelating agent to chelate calcium ions in the sample or which are contained during separation processes. The above insect plasma and hemocyte lysate can be prepared with a sufficient amount of chelating agent to chelate calcium ions in the sample or which are contained during separation processes.

In the detection method of β-1,3-glucan according to the present invention, the specimen to be tested may be animals including humans or any the environment. For example, the fungal infection can be diagnosed by collecting blood from a specimen. In another example, water is collected from the environment and can be tested an infection by microorganisms, like fungi, that have β-1,3-glucan as a cell well component in the cultivating industry.

To increase the specificity of the diagnosis of the infection by microorganisms that have β-1,3-glucan as a cell wall component, pretreatment for eliminating lipopolysaccharide that may exist in a specimen sample can be carried out, if necessary. For instance, the influence of lipopolysaccharide can be eliminated by treating the specimen sample with materials such as polymyxin that can bind specifically with or precipitate lipopolysaccharide.

Any determination method of phenoloxidase activity known in the field can be used in its present condition or with some modifications as the method of determining phenoloxidase activity that can be used as a diagnostic method of fungal infection in the present invention. For instance, the phenoloxidase activity can be determined easily at the early stage of the fungal infection by measuring the absorbance of the color developed by the 4-methylcatechol/4-hydroxyproline ethyl ester (4-MC/4-HP) or from the melanin formation reaction using dopamine Also the present invention relates to a diagnostic kit for detecting β-1,3-glucan. The diagnostic kit for detecting β-1,3-glucan contains the composition that exhibits the phenoloxidase activity by β-1,3-glucan in the presence of calcium ions. For example, the composition that exhibits the phenoloxidase activity by β-1,3-glucan in the presence of calcium ion is a composition that can be prepared by collecting a sample comprising plasma or a mixture of plasma and hemocyte lysate from an insect; treating said sample with a solvent or buffer solution containing a sufficient amount of a chelating agent to chelate calcium ions existing in said sample and in the present separation process to obtain fractions therefrom; and selecting fractions exhibiting phenoloxidase activity by β-1,3glucan in the presence of calcium ions from the obtained fractions.

The buffer solution and the method to determine the phenoloxidase activity used in the present invention are as follows.

Anticoagulation buffer solution (pH 5.5): NaCl 15 mM, trisodium citrate 136 mM, citric acid 26 mM, EDTA 20 mM β-1,3-glucan solution: a solution prepared by mixing 10 μl of the solution, made by mixing 10 mg of β-1,3-glucan (curdlan, Wako Pure Chemical Industries, Ltd., Japan) in 1 ml of 0.1 N NaOH, and 990 μl of 20 mM Tris buffer solution (pH 8.0)

4-MC/4-HP Color Development Reaction

To 10 μl of β-1,3-glucan solution diluted to predetermined concentration, 30 μl of phenoloxidase composition was added and pre-reacted for 5 min at 30° C. To this mixture, 437.5 μl of 20 mM Tris buffer solution (pH 7.5), 5 μl of 1M $CaCl_2$, 2 μl of 250 mM 4-methylcatechol (MC) and 16 μl of 62.5 mM 4-hydroxyproline ethyl ester (HP) were added to make the total volume to 500 μl and reacted for 30 min at 30° C. To this reaction mixture, 500 μl of 20% acetic acid was added to terminate the reaction. And the absorbance was measured at 520 nm.

Melanin Formation Reaction

To 10 μl of diluted β-1,3-glucan solution, 30 μl of phenoloxidase composition was added and pre-reacted for 10 min at 30° C. After adding 405 μl of 20 mM Tris buffer solution (pH 8.0), 5 μl of 1M $CaCl_2$ and 50 μl of 10 mM dopamine solution, the mixture was reacted for 60 min at 30° C. Standard curve was formed by measuring absorbance at 400 nm. The plasma obtained by centrifuging the blood collected from a specimen was used as a sample and treated by identical procedures as described above to determine absorbance at 400 nm. The amount of β-1,3-glucan in the sample can be determined from the standard curve.

EXAMPLES

The present invention is further illustrated by way of the following Examples, but by no means limited thereto.

Example 1

The larvae of *Tenebrio molitor* were anesthetized on ice. Three drops of hemolymph were collected in each of larvae by inserting a 25 G needle connected to a 5 ml sterile syringe containing anticoagulation buffer solution into the first segment from the head. After centrifuging 60 ml of collected hemolymph for 4 h at 4° C. at 203,006 g, 55 ml of sample was obtained by filtering (0.45 μm) the supernatant to eliminate the impurities This sample was concentrated to 3 ml by ultrafiltration (cut off: 10,000). After packing Toyopearl HW-55S resin into a 1×50 cm column, the column was washed with a sufficient amount of anticoagulation buffer solution. After loading the concentrated sample into the column, an anticoagulation buffer solution was added and eluted at 0.18 ml/min flow rate. The eluant was collected to the volume of 3.8 ml each, and the absorbance was measured at 280 nm to check the protein concentration. By performing the 4-MC/4-HP color development reaction using β-1,3-glucan, the fractions that developed color in the presence of β-1,3-glucan were collected to obtain 3.8 ml of primarily purified phenoloxidase composition. Using the primarily purified phenoloxidase composition, the detection activity of β-1,3-glucan was identified in the presence or absence of $Ca^{2+}$.

Figure 1:
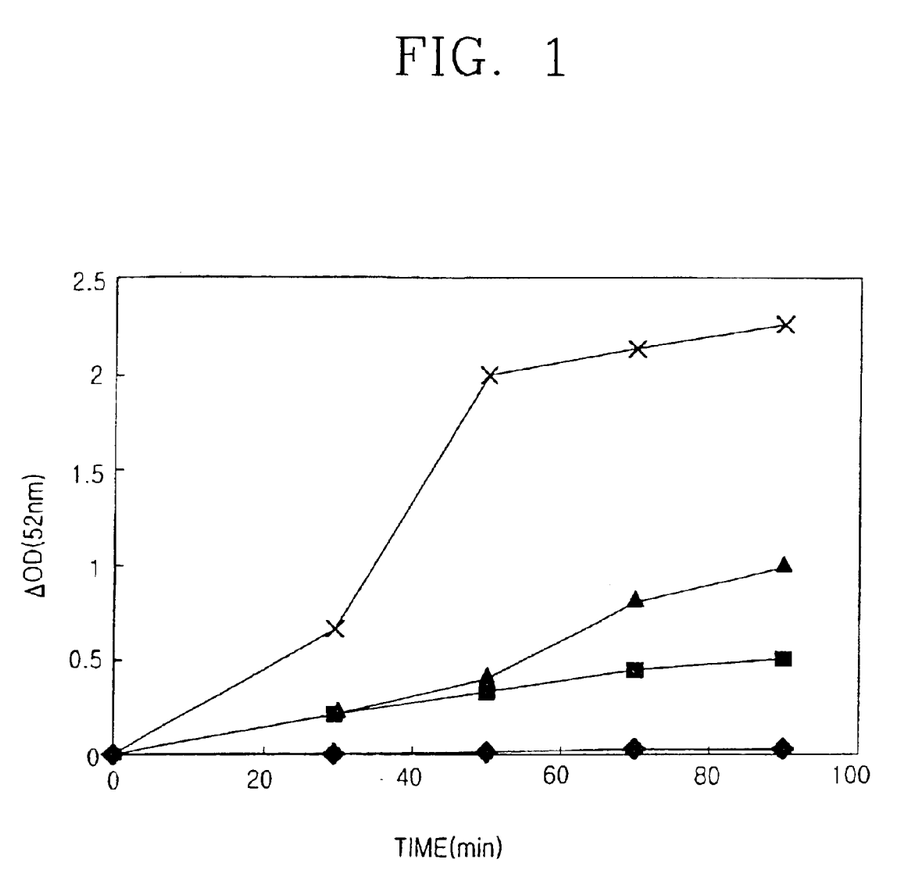
FIG. 1 Is a graph showing the phenoloxidase activity of the phenoloxidase composition isolated from the hemolymph of *Tenebrio molitor* depending on the reaction time in the presence of calcium ions and β-1,3-glucan.

After loading 3.8 ml of the primarily purified phenoloxidase composition into the identical column as described above, an anticoagulation buffer solution was added and eluted at 0.16 ml/min flow rate. The eluant was collected to the volume of 3 ml each, and the absorbance was measured at 280 nm to check the protein concentration. By performing the 4-MC/4-HP color development reaction using β-1,3-glucan, the fractions that developed color in the presence of β-1,3-glucan were collected as secondarily purified phenoloxidase composition and it was considered as the final composition. By setting the final $Ca^{2+}$ concentration to 0 mM or 5 mM, the 4-MC/4-HP color development reaction was carried out by using 10 μl of 100 ng/ml of β-1,3-glucan solution and the phenoloxidase composition. The result was obtained as a function of the reaction time and is shown in FIG. 1 ((-♦-: buffer solution, -■-: phenoloxidase composition, -▲-: phenoloxidase composition+$Ca^{2+}$, -×-: phenoloxidase composition+$Ca^{2+}$+β-1,3-glucan). From the Figure, it can be seen that the phenoloxidase composition shows the phenoloxidase activity in the presence of β-1,3-glucan.

Figure 2:
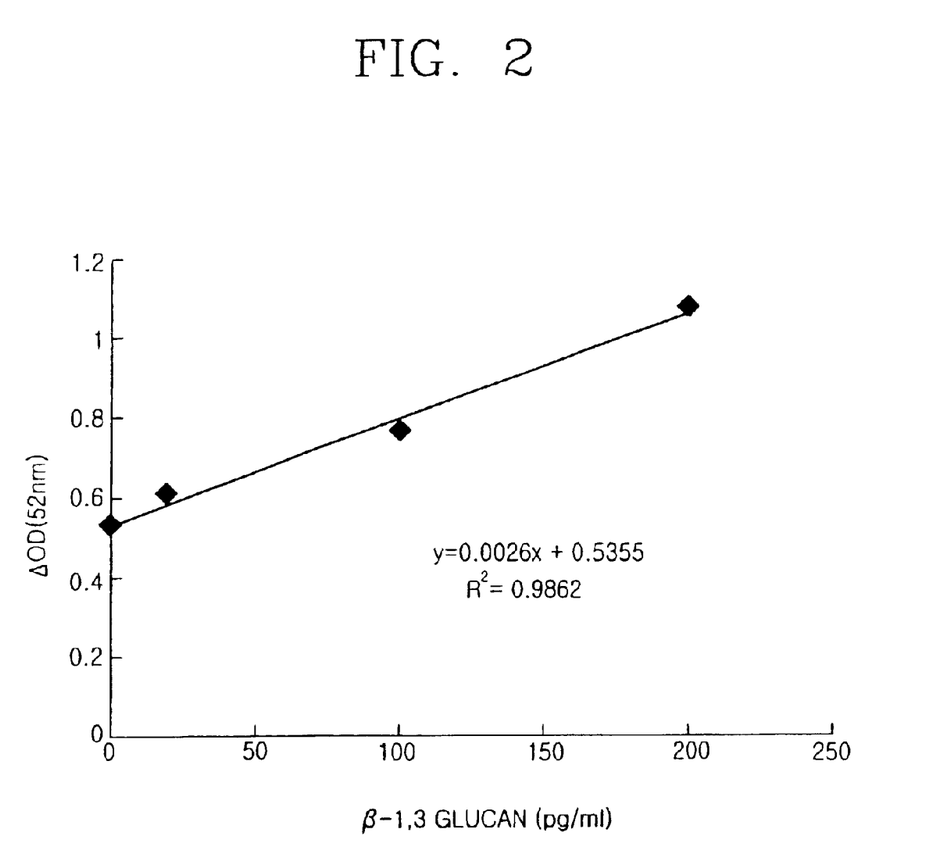
FIG. 2 is a standard curve of the phenoloxidase activity of the phenoloxidase composition isolated from the hemolymph of *Tenebrio molitor* depending on the concentration of β-1,3-glucan.

The standard curve was obtained by measuring the phenoloxidase activity of the phenoloxidase composition as a function of β-1,3-glucan concentration. The absorbance was measured at 520 nm after a one hour reaction at 30° C. by using the above described color development reaction in the β-1,3-glucan concentration range between 0 and 200 pg/ml The result is shown in FIG. 2. From the figure, it is obvious that an infinitesimal amount of β-1,3-glucan can be detected since the correlation coefficient between the concentration and activity is 0.9862.

Example 2

Figure 3:
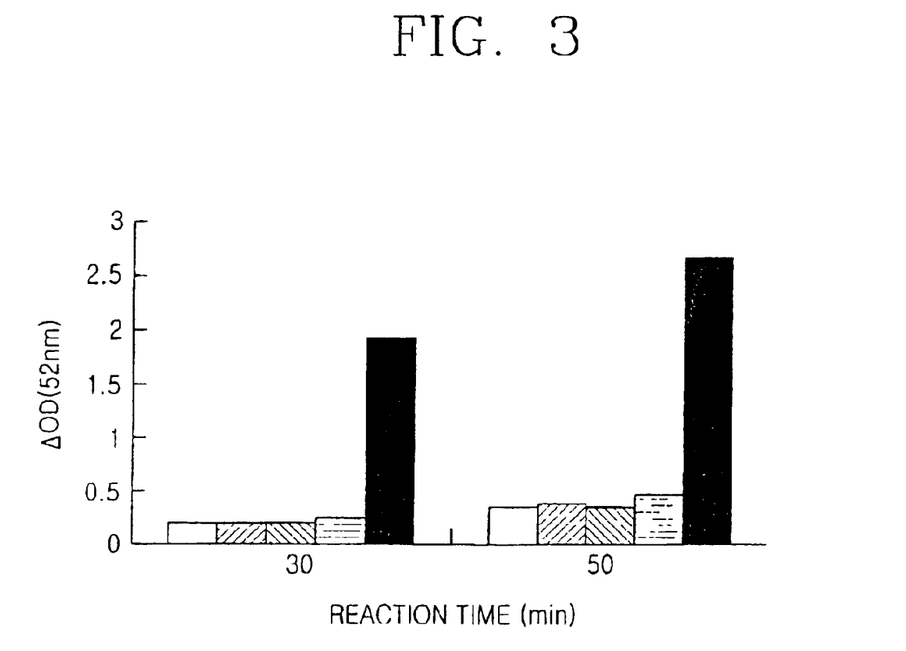
FIG. 3 is a graph examining the detection specificity in relative to lipopolysaccharide of the phenoloxidase composition isolated from the hemolymph of *Tenebrio molitor;*

To check whether the phenoloxidase composition in Example 1 had the specificity to β-1,3-glucan, the phenoloxidase activity was determined by using lipopolysaccharide and peptidoglycan. Lipopolysaccharide (Sigma Chemical Company) and peptidoglycan (Sigma) were each suspended in 50 mM of Tris buffer solution (pH 7.0). As substrates, peptidoglycan suspension was used as it is and lipopolysaccharide suspension was used after sonication for 2–3 min. By using lipopolysaccharide at 200 pg/ml, 20 ng/ml, 20 μg/ml concentrations as substrates, the color development reaction with 4-MC/4-MP solution was carried out by using phenoloxidase composition at 5 mM $Ca^{2+}$. The color was compared with the color developed from the experiment using 20 ng/ml of β-1,3-glucan as a substrate. The result is shown in FIG. 3 (□: negative control having phenoloxidase composition and $Ca^{2+}$ (A hereinafter), ▨: A+lipopolysaccharide 200 pg/ml, ▩: A+lipopolysaccharide 20 ng/ml, ▤: A+lipopolysaccharide 20 μg/ml, ■ : A+β-1,3-glucan 20 ng/ml (positive control)).

Figure 4:
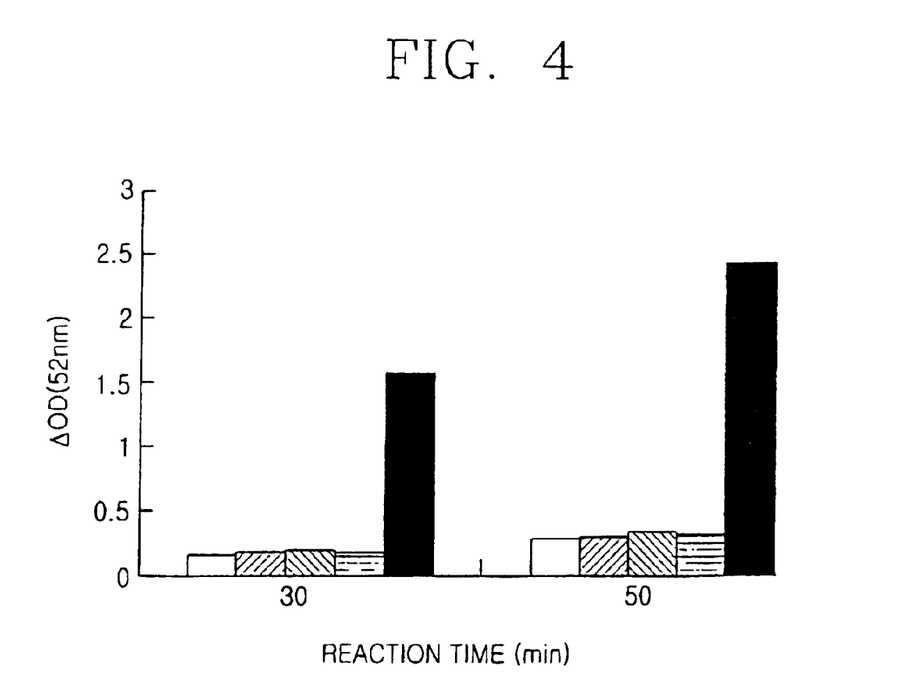
FIG. 4 is a graph examining the detection specificity in relative to peptidoglycan of the phenoloxidase composition isolated from the hemolymph of *Tenebrio molitor;*

The phenoloxidase activity was also determined with peptidoglycan under identical experimental conditions as above. The result is shown in FIG. 4 (□: negative control having phenoloxidase composition and $Ca^{2+}$ (A hereinafter), ▨: A+peptidoglycan 200 pg/ml, ▩: A+peptidoglycan 20 ng/ml, ▤: A+peptidoglycan 20 μg/ml, ■ : A+β-1,3-glucan 20 ng/ml (positive control)).

As described above, the phenoloxidase activity does not appear at high concentration, 20 ug/ml of lipopolysaccharide and peptidoglycan even if the reaction time is increased. Therefore the phenoloxidase composition of the present invention can detect β-1,3-glucan specifically.

Comparative Example 1

Larvae of *Tenebrio molitor* were anesthetized on ice. Three drops of hemolymph were collected from each larva by inserting a 25 G needle connected to a 5 ml sterile syringe containing anticoagulation buffer solution into the first segment from the head. After centrifuging 85 ml of the collected hemolymph for 5 min at 4° C. at 372 g, the supernatant and the precipitate were obtained as plasma and hemocytes, respectively. After centrifuging 60 ml of the collected plasma for 4 h at 4° C. at 203,006 g and filtering (0 45 μm) the supernatant to eliminate impurities, 58 ml of the supernatant was obtained. This sample was concentrated to 3 ml by ultrafiltration (cut off: 10,000). After packing Toyopearl HW-55S resin into a 1×50 cm column, the column was washed with anticoagulation buffer solution. After loading the concentrated sample into the column, anticoagulation buffer solution was added and eluted at 0.18 ml/min flow rate. The eluant was collected to the volume of 3.8 ml each, and the absorbance was measured at 280 nm to check the protein concentration By performing the 4-MC/4-HP color development reaction using β-1,3-glucan, the fraction that developed color in the presence of β-1,3-glucan was collected to obtain 3.8 ml of phenoloxidase composition of primary purified plasma.

In the meantime, the above precipitated hemocytes were washed with anticoagulation buffer solution and centrifuged to remove the plasma portion.

This procedure was repeated 3 times. To disrupt the hemocytes completely, the cells were sonicated and centrifuged for 5 min at 4° C. at 372 g to obtain 3 ml of supernatant as the hemocyte lysate.

Figure 5:
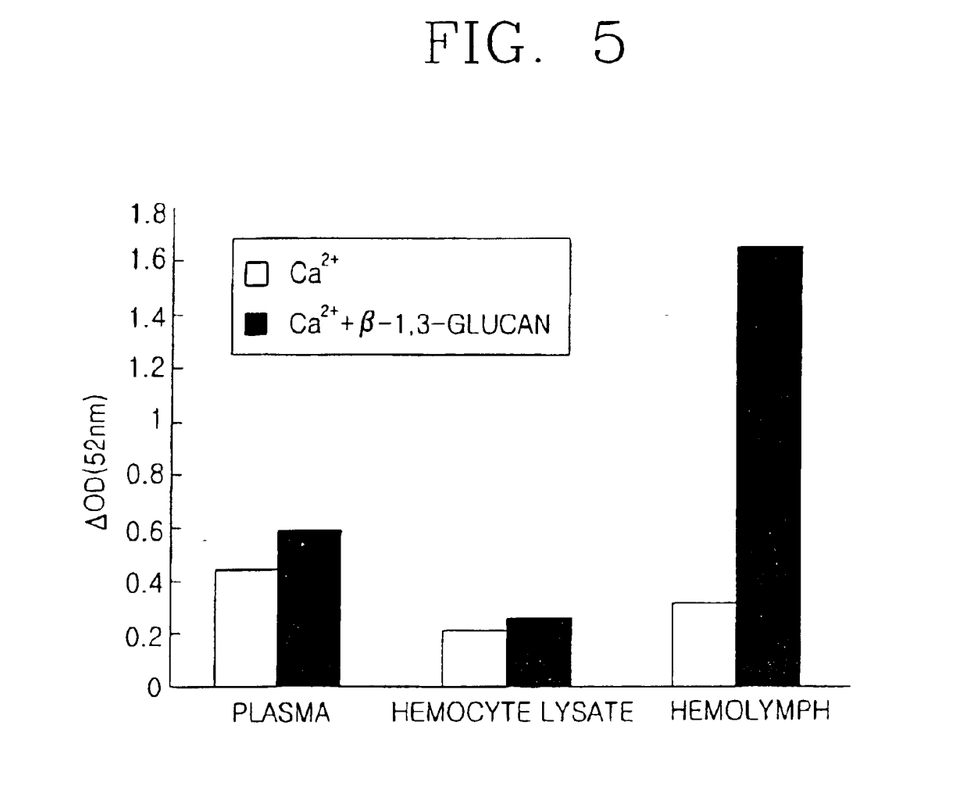
FIG. 5 is a graph comparing the phenoloxidase activity induced by β-1,3-glucan in each composition obtained from plasma, hemocyte lysate and hemolymph of *Tenebrio molitor;*

The β-1,3-glucan (2 ng/ml of concentration) detection abilities of the phenoloxidase composition of partially purified plasma, hemocyte lysate and the phenoloxidase composition of primarily purified hemolymph of Example 1 were compared by using the same amount (400 μg) of proteins in the presence of $Ca^{2+}$ ions. The result is shown in FIG. 5. It can be seen from the Figure that the phenoloxidase composition obtained from the hemolymph can detect β-1,3-glucan.

Figure 6:
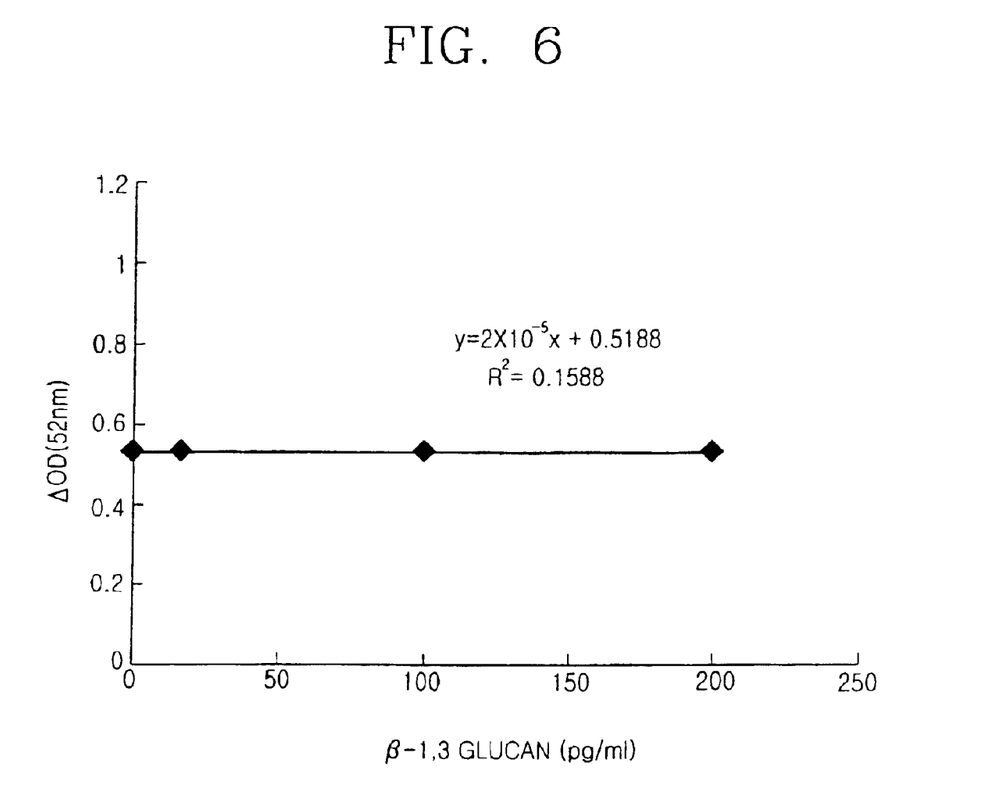
FIG. 6 is a graph of the phenoloxidase activity of the phenoloxidase composition isolated from the plasma of *Tenebrio molitor* depending on the concentration of β-1,3-glucan.

On the other hand the above-described phenoloxidase composition derived from plasma was used to check the detection ability for β-1,3-glucan as a function of β-1,3-glucan concentrations. As shown in FIG. 6, there was no correlation between β-1,3-glucan concentration and phenoloxidase activity when the phenoloxidase composition derived from only plasma was used.

Example 3

To check whether the phenoloxidase composition had specificity to β-1,3-glucan, melanin formation reactions were carried out using various sugars according to the method described above. The results of measuring the absorbance at 400 nm to determine the amount of produced melanin showed that melanin production was observed significantly in the presence of β-1,3-glucan only. The results are summarized in Table 1.

TABLE 1

| Saccharide | Bond type | Absorbance (400 nm) |
|---|---|---|
| D (+) glucose | | 0.211 |
| Cellulose | β-1,4 | 0.240 |
| Maltose | α-1,4 | 0.237 |
| Dextran | α-1,6 | 0.290 |
| Laminarin | β-1,3, β-1,6 | 0.292 |
| Zymosan | β-1,3 | 3.616 |
| Curdlan | β-1,3 | 3.352 |
| 20 mM Tris (pH 8.0) | | 0.208 |

Example 4

After centrifuging 50 ml of hemolymph collected from larvae of *Holotrichia diomphalia* for 20 min at 4° C. at 420 g, the supernatant and the precipitate were obtained as plasma and hemocytes, respectively First, the hemocyte precipitate (5 ml) was sonicated after adding 5 ml of 50 mM Tris buffer solution/1 mM EDTA (pH 6.5), then centrifuged for 20 min at 4° C. at 22,000 g to obtain the supernatant as the hemocyte lysate.

In the meantime, after centrifuging 50 ml of collected plasma for 4 h at 4° C. at 203,006 g, the supernatant was concentrated to 3 ml by ultrafiltration (cut off: 10,000). After packing Toyopearl HW-55S resin into a 1×50 cm column, the column was equilibrated with 50 mM Tris buffer solution/20 mM EDTA (pH 6.5). After loading the concentrated sample into the column, 50 mM Tris buffer solution/20 mM EDTA (pH 6.5) was added and eluted at 0.16 ml/min flow rate. The eluant was collected to the volume of 3.2 ml each, the absorbance was measured at 280 nm to check the protein concentration and fractions that developed color with 4-MC/4-HP in the presence of 5 mM $Ca^{2+}$ were collected. Among these fractions, fractions having phenoloxidase activity in the presence of the above hemocyte lysate and β-1,3-glucan were collected as partially purified plasma solution (3.2 ml).

Figure 7:
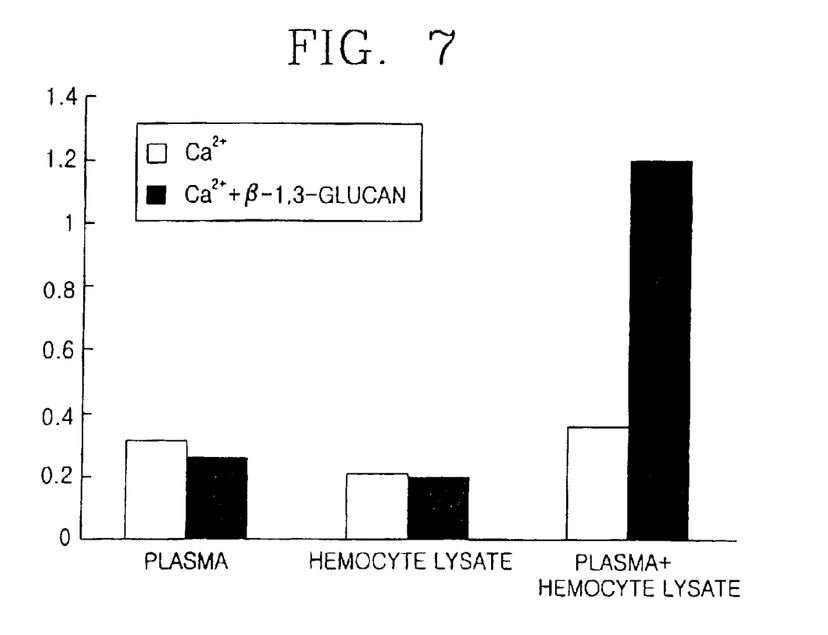
FIG. 7 is a graph comparing phenoloxidase activity induced by β-1,3-glucan in each phenoloxidase composition obtained from the plasma, hemocyte lysate and their mixture of larva of *Holotrichia diomphalia;*

The β-1,3-glucan detection abilities of partially purified plasma solution (protein content: 25 μg), the above hemocyte lysate (protein content: 175 μg), and the phenoloxidase composition made by mixing these two (protein content ratio 25 μg: 175 μg) were determined. The results are shown in FIG. 7. The 4-MC/4-HP color development reaction was carried out for 30 min by setting the final $Ca^{2+}$ concentration to 5 mM, and by using 10 μl of 0.1 μg/ml of β-1,3-glucan. The mixture of partially purified plasma solution and the hemocyte lysate exhibited the phenoloxidase activity in the presence of β-1,3-glucan.

Figure 8:
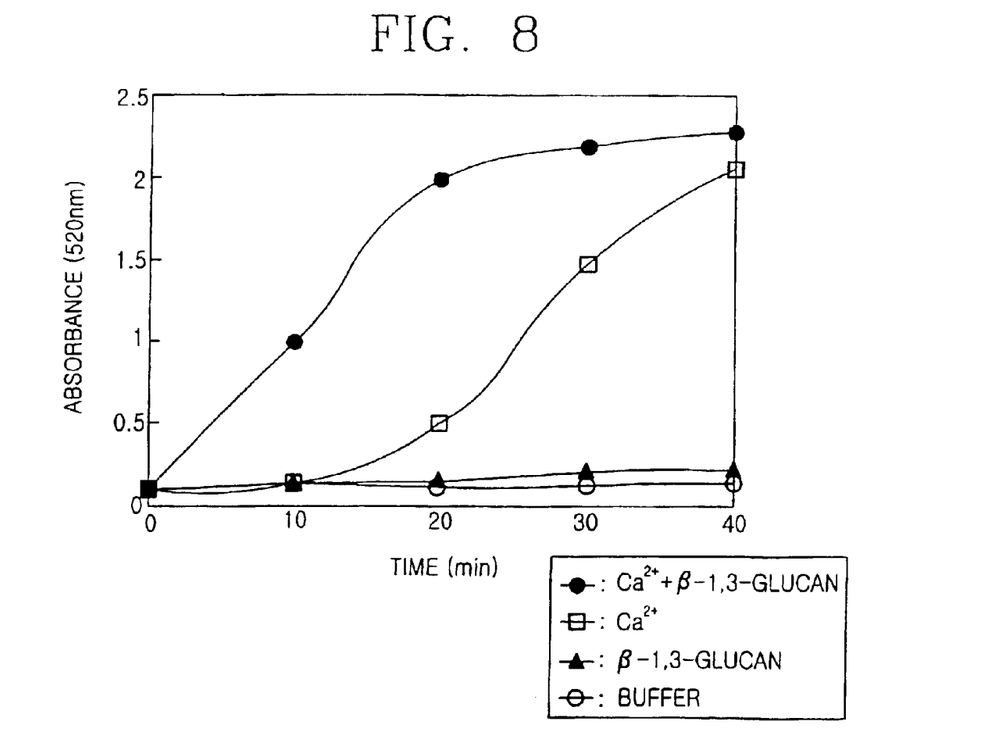
FIG. 8 is a graph showing the phenoloxidase activity of the mixture of phenoloxidase composition isolated from the plasma of larvae of *Holotnchia diomphalia* and hemocyte lysate according to the reaction time in the presence of calcium ions and β-1,3-glucan.

Also, FIG. 8 shows the β-1,3-glucan detection ability using the above phenoloxidase composition under identical experimental conditions as above as a function of reaction time (●-●: Final calcium ion concentration 5 mM+β-1,3-glucan 2 μg/ml, □-□: Final calcium ion concentration 5 mM, ○-○: 20 mM Tris buffer solution, ▲-▲:β-1,3-glucan 2 μg/ml). The phenoloxidase activity was observed for calcium ions and for β-1,3-glucan in the presence of calcium ions.

Example 5

Blood was collected from 11 healthy adult males and females and 50 hospitalized cancer patients. After treating the collected blood with heparin, the blood was centrifuged to obtain plasma as samples for detecting β-1,3-glucan.

Figure 9:
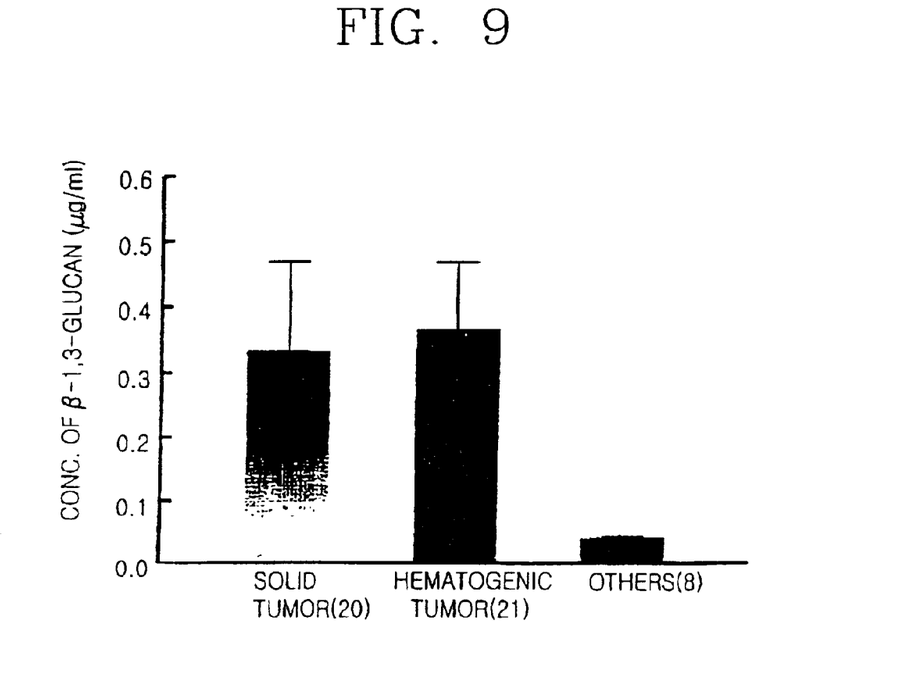
FIG. 9 is a graph showing the result of β-1,3-glucan detection using the phenoloxidase composition in the blood of cancer patients.
Figure 10:
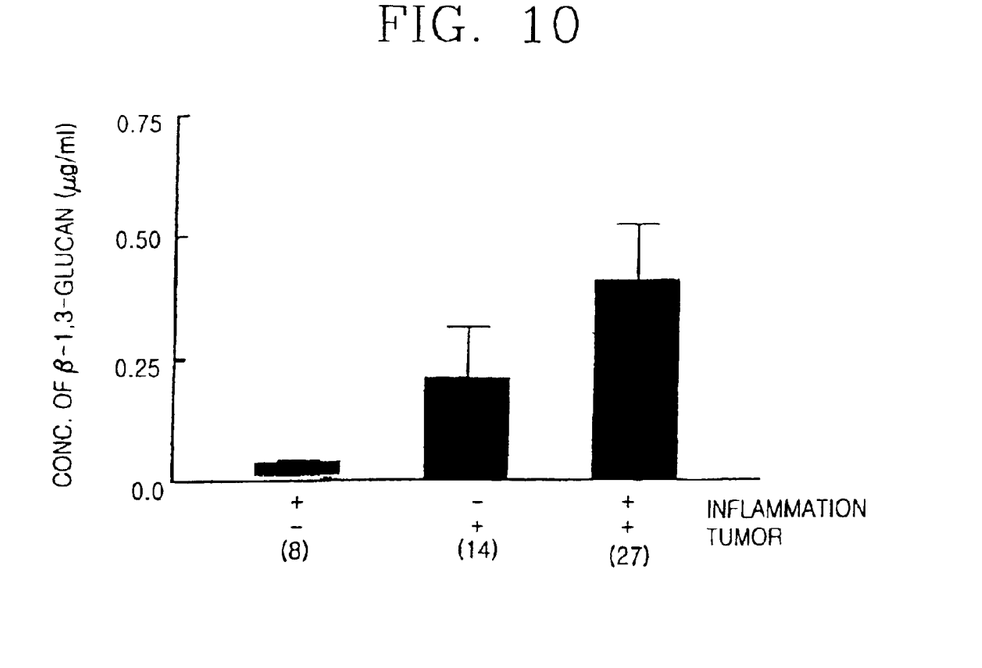
FIG. 10 is a graph showing the result of β-1,3-glucan detection using the phenoloxidase composition in the blood of tumor and inflammatory disease patients.

To 10 μl of the plasma obtained from the patients, 10 μl of the partially purified phenoloxidase composition as prepared in Example 1 was added to carry out 4-MC/4-HP color development reaction. The absorbance was measured at 520 nm, and the amount of β-1,3-glucan in the sample was calculated from a standard curve. The amount of β-1,3-glucan in the plasma collected from the healthy male and female subjects (11 persons) was negligible, The β-1,3-glucan concentrations in the solid tumor and hematogenic tumor patients who were immuno-compromised patients due to undergoing anticancer treatment were remarkably higher than those in the inflammatory disease patients (in FIG. 9, the numbers in parentheses are the repeated numbers of the experiment, and the concentration of β-1,3-glucan is expressed as μg/ ml serum and represents the value of average±SEM) The patients categorized as 'Others' in FIG. 9 were those with inflammatory disease without tumors As shown in FIG. 10, only a negligible amount of β-1,3-glucan was detected in the inflammatory disease patients but the amounts of β-1,3-glucan were much larger in the patients who had both tumor and inflammatory disease (The numbers in parentheses are the repeated numbers of the experiment, and the concentration of β-1,3-glucan is the value of average±SEM). In the latter, it is assumed that the incidence of fungal infection was higher for the patients who had both tumor and inflammatory disease than those who had tumor disease only since the immune system of such patients does not function properly.

Figure 11:
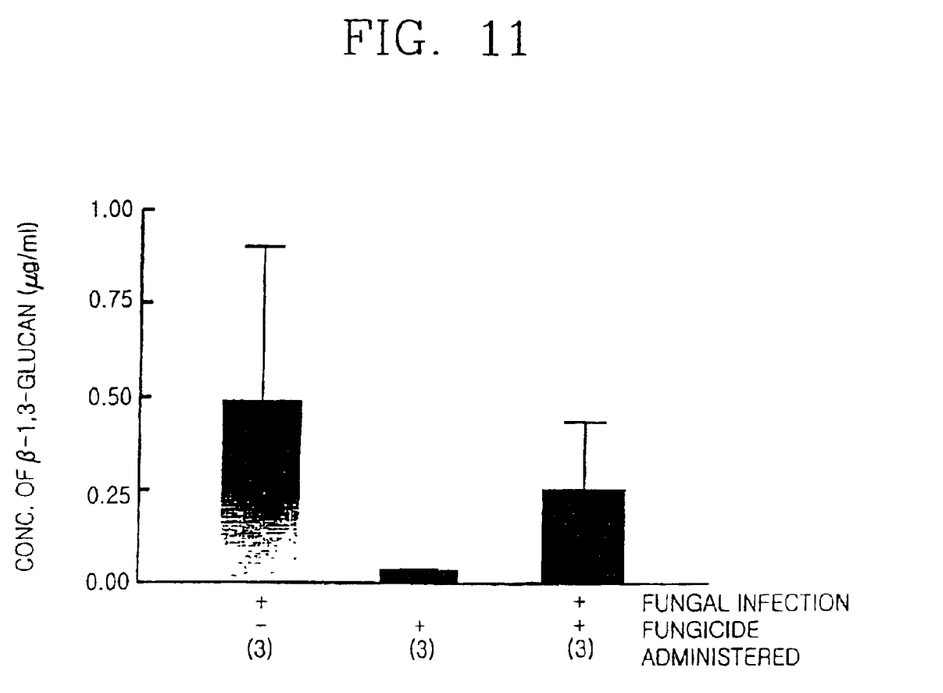
FIG. 11 is a graph showing the result of β-1,3-glucan detection using the phenoloxidase composition in the blood of Candidiasis patients.

In the case of the patients who had been confirmed to be Candidiasis, the concentration of β-1,3-glucan was much higher, but those who were under antifungal treatment had lower concentration of β-1,3-glucan (in FIG. 11, the numbers in parentheses are the repeated numbers of the experiment and the concentration of β-1,3-glucan is the value of average±SEM). Therefore, it was possible to diagnose the fungal infection by measuring the concentration of β-1,3-glucan in a sample by using the composition of the present invention.

INDUSTRIAL APPLICABILITY

According to the present invention, the infection by microorganisms that have β-1,3-glucan as a cell wall component can be diagnosed at an early stage of the infection For an immuno-compromised patient, the mortality can then be lowered by administering appropriate antibiotics or antifungal drugs since it is possible to diagnose infection by microorganisms that have β-1,3-glucan at an early stage of the infection. It will become also possible to reduce the damage in the cultivating industry by taking appropriate actions at an early stage after the fungal infection.

What is claimed is:

1. A composition for detecting β-1,3-glucan in the presence of calcium ions, prepared by the method comprising:
   (i) collecting a sample comprising a mixture of plasma and hemocyte lysate from *Tenebrio molitor* or *Holotrichia diomphalia;*
   (ii) purifying said sample by column chromatography using a solvent or buffer solution containing a sufficient amount of a chelating agent to chelate calcium ions present in said sample to obtain fractions therefrom; and
   (iii) selecting fractions exhibiting phenoloxidase activity by β-1,3-glucan in the presence of calcium ions from the obtained fractions.

2. A composition for detecting β-1,3-glucan according to claim 1 wherein the composition detects β-1,3-glucan concentrations as low as 20 pg/ml in the presence of calcium ions.

3. A composition for detecting β-1,3-glucan exhibiting phenoloxidase activity by β-1,3-glucan in the presence of calcium ions, said composition prepared by:
   (i) treating *Tenebric molitor* or *Holotrichia diomphalia* plasma with a solvent or buffer solution containing a sufficient amount of a chelating agent to chelate calcium ions present in the plasma and
   (ii) separating said chelated plasma by chromatography to obtain fractions from said chelated plasma;
   (iii) adding hemocyte lysate or partially purified hemocyte lysate to said fractions to form lysate treated fractions, and
   (iv) selecting lysate treated fractions exhibiting phenoloxidase activity by β-1,3-glucan in the presence of calcium ions.

* * * * *